(12) United States Patent
Ito

(10) Patent No.: US 11,957,140 B2
(45) Date of Patent: Apr. 16, 2024

(54) METHOD FOR PREPARING A COMPOSITION BASED ON LEGUME PROTEINS

(71) Applicant: ROQUETTE FRERES, Lestrem (FR)

(72) Inventor: Goichi Ito, Tokyo (JP)

(73) Assignee: Roquette Freres, Lestrem (FR)

( * ) Notice: Subject to any disclaimer, the term of this patent is extended or adjusted under 35 U.S.C. 154(b) by 702 days.

(21) Appl. No.: 16/644,209

(22) PCT Filed: Sep. 10, 2018

(86) PCT No.: PCT/FR2018/052208
§ 371 (c)(1),
(2) Date: Mar. 4, 2020

(87) PCT Pub. No.: WO2019/048804
PCT Pub. Date: Mar. 14, 2019

(65) Prior Publication Data
US 2021/0068434 A1    Mar. 11, 2021

(30) Foreign Application Priority Data
Sep. 11, 2017  (FR) ...................................... 17 58365

(51) Int. Cl.
| A23L 33/185 | (2016.01) |
| A23J 3/14 | (2006.01) |
| A23L 2/66 | (2006.01) |
| A23L 11/30 | (2016.01) |
| A23L 29/00 | (2016.01) |
| A23L 33/00 | (2016.01) |
| C07K 14/415 | (2006.01) |

(52) U.S. Cl.
CPC .................. *A23L 11/35* (2016.08); *A23J 3/14* (2013.01); *A23L 2/66* (2013.01); *A23L 29/015* (2016.08); *A23L 33/185* (2016.08); *A23L 33/40* (2016.08); *C07K 14/415* (2013.01); *A23V 2002/00* (2013.01)

(58) Field of Classification Search
CPC .......... A23L 2/66; A23L 33/185; A23L 11/65; A23L 11/30; A23L 11/35; A23L 11/31
See application file for complete search history.

(56) References Cited

U.S. PATENT DOCUMENTS

| 4,241,100 A | 12/1980 | Wakana et al. |
| 2007/0014910 A1* | 1/2007 | Altemueller ............. A23L 2/02 426/590 |

FOREIGN PATENT DOCUMENTS

| JP | 2001245633 A | 9/2001 |
| WO | 2010/092778 A1 | 8/2010 |
| WO | 2012/081971 A1 | 6/2012 |
| WO | 2017/102257 A1 | 6/2017 |
| WO | 2017/102258 A1 | 6/2017 |

OTHER PUBLICATIONS

Soybean, Britannica Online Encyclopedia, retrieved online Aug. 23, 2023. https://www.britannica.com/plant/soybean (Year: 2023).*
The English translation of the International Search Report, dated Nov. 21, 2018, in the corresponding PCT Appl. No. PCT/FR2018/052208.
C-L Heydley et al., "Developing novel pea starches" Proceedings of the Symposium of the Industrial Biochemistry and Biotechnology Group of the Biochemical Society, 1996, pp. 77-87.
Database GNPD [Online] Mintel; Jun. 2009 (Jun. 2009), Anonymous: "Body Active", XP002775718, Database accession No. 1126898, the whole document.
Database GNPD [Online] Mintel; Aug. 2014 (Aug. 2014), Anonymous: "Unflavored beverage", XP002775719, Database accession No. 2607025, the whole document.
Database GNPD [Online] Mintel; Jan. 2016 (Jan. 2016), Anonymous: "Food for special medical purposes", XP002775720, Database accession No. 3675657, the whole document.
Database GNPD [Online] Mintel; Feb. 2015 (Feb. 2015), Anonymous: "Nutritionally complete drink for enteral nutrition", XP002775721, Database accession No. 2802807, the whole document.
Database GNPD [Online] Mintel; Feb. 2017 (Feb. 2017), Anonymous: "Tomato diet soup", XP002775722, Database accession No. 4636429, the whole document.
Schindler Sabrina et al: "Improvement of the Aroma of Pea (*Pisum sativum*) Protein Extracts by Lactic Acid Fermentation", Food Biotechnol, Dekker, New York, NY, USA, vol. 26, No. 1, Jan. 1, 2012 (Jan. 1, 2012), pp. 58-74, XP009177299.
The English translation of the Chinese Office Action, dated Oct. 19, 2022, in the related Chinese Appl. No. 2018800587553.3.
Wang Shuying, "Discuss the problems in the production process of soymilk", Chinese condiments, Oct. 1994 Issue 10, pp. 25-27. (Machine-generated translation included).

* cited by examiner

*Primary Examiner* — Hong T Yoo

(57) ABSTRACT

The present invention relates to a method for preparing a composition with reduced bitterness on the basis of legume proteins, a composition which can be obtained by said method, and uses of same particularly in the agri-food industry and more particularly in the preparation of food formulations.

3 Claims, No Drawings

METHOD FOR PREPARING A COMPOSITION BASED ON LEGUME PROTEINS

CROSS-REFERENCE TO RELATED APPLICATIONS

This application is a National Stage Application of PCT/FR2018/052208 filed Sep. 10, 2018, which claims priority from French Patent Application No. 17 58365, filed on Sep. 11, 2017. The priority of said PCT and French Patent Application are claimed. Each of the prior mentioned applications is hereby incorporated by reference herein in its entirety.

FIELD OF THE INVENTION

The present invention relates to a process for preparing a reduced-bitterness composition based on leguminous-plant proteins, to a composition that can be obtained by means of said process, and also to the uses thereof, in particular in the food-processing field and most particularly for the preparation of food formulations.

PRIOR ART

Along with carbohydrates and lipids, proteins constitute a significant part of our diet. Daily protein requirements are generally between 12% and 20% of food intake.

The proteins consumed are generally either of animal origin, for instance meats, fish, eggs or else milk products, or of plant origin, for instance cereals, oleaginous plants or else leguminous plants.

However, in industrialized countries, protein intakes are mainly in the form of proteins of animal origin. However, many studies demonstrate that excessive consumption of proteins of animal origin to the detriment of plant proteins is one of the causes of increase in cancers and cardiovascular diseases.

Moreover, animal proteins have many disadvantages, both in terms of their allergenicity, concerning in particular proteins from milk or eggs, and in environmental terms in relation to the damaging effects of intensive farming.

Thus, as an alternative, manufacturers have gradually turned to plant proteins. Indeed, it is known practice to use plant proteins in order to replace all or some of the proteins of animal origin in foods.

Such a replacement is not always easy because plant proteins have functional properties that are different from animal proteins. The functional properties are the physical or physicochemical properties which have an effect on the sensory qualities of the food systems generated during technological transformations, storage or domestic culinary preparations.

Among the plant proteins, it is for example known practice to use leguminous-plant proteins. With regard to milk proteins, although they are of strong nutritional advantage, their high cost much too often constitutes an impediment to large-scale use in the food-processing field. Thus, milk proteins can be replaced with leguminous-plant proteins.

One drawback of certain plant proteins, in particular leguminous-plant proteins, is the fact that they are not neutral in terms of taste, thus causing a bitter taste in the products into which they are incorporated.

Thus, in order to promote the replacement of animal proteins with plant proteins in the food-processing industry, there is a need to have a solution which makes it possible in particular to decrease the bitterness of plant proteins, and particularly leguminous-plant proteins, including most particularly pea proteins.

The applicant has thus, to its credit, developed a process which makes it possible to obtain a composition based on leguminous-plant proteins, said composition having a reduced bitterness, or even completely masked bitterness.

SUMMARY OF THE INVENTION

A subject of the present invention is thus a process for preparing a reduced-bitterness composition based on leguminous-plant proteins, comprising the following steps:
  preparing an aqueous solution or suspension comprising both leguminous-plant proteins and sodium citrate,
  heat-sterilizing said aqueous solution or suspension comprising leguminous-plant proteins and sodium citrate at a temperature of between 125° C. and 134° C. for a period of between 90 and 300 seconds, or at a temperature of between 135° C. and 144° C. for a period of between 90 and 210 seconds, or at a temperature of between 145° C. and 155° C. for a period of between 20 and 90 seconds.

The process according to the invention is particularly advantageous since it makes it possible to provide a composition based on leguminous-plant proteins, more particularly on pea proteins, which exhibits a decrease in the bitter taste generally characteristic of leguminous-plant proteins.

The present invention also relates to a reduced-bitterness composition based on leguminous-plant proteins, more particularly on pea proteins, which can be obtained by means of the process according to the invention.

Finally, the present invention relates to the use of said reduced-bitterness composition in the food-processing industry, and more particularly for preparing food formulations.

DETAILED DESCRIPTION

A subject of the present invention is thus a process for preparing a reduced-bitterness composition based on leguminous-plant proteins, comprising the following steps of:
  preparing an aqueous solution or suspension comprising leguminous-plant proteins and sodium citrate,
  heat-sterilizing said aqueous solution or suspension comprising leguminous-plant proteins and sodium citrate at a temperature of between 125° C. and 134° C. for a period of between 90 and 300 seconds, or at a temperature of between 135° C. and 144° C. for a period of between 90 and 210 seconds, or at a temperature of between 145° C. and 155° C. for a period of between 20 and 90 seconds.

For the purposes of the present invention, the term "leguminous plants" is intended to mean any plants belonging to the families Caesalpiniaceae, Mimosaceae or Papilionaceae, such as alfalfa, clover, lupin, pea, bean, broad bean, horse bean or lentil, and more particularly pea.

For the purposes of the present invention, the term "reduced-bitterness" is intended to mean a composition for which the perception of the bitter taste is decreased, or even completely masked.

Surprisingly, the inventors have noted that the process according to the invention, through the combination of the use of sodium citrate and of a heat-sterilization step, at a temperature between 125° C. and 134° C. for a period of between 90 and 300 seconds, or at a temperature between 135° C. and 144° C. for a period of between 90 and 210 seconds, or at a temperature of between 145° C. and 155° C. for a period of between 20 and 90 seconds, makes it possible to reduce, or even completely mask, the bitterness of a composition based on leguminous-plant proteins. The sterilization schedules applied to the aqueous solution or suspension comprising leguminous-plant proteins and sodium citrate can also be defined by a number obtained by multiplying the temperature applied in degrees Celsius and the contact time expressed in seconds. The number obtained, which thus represents the amount of energy applied to the aqueous solution or suspension comprising leguminous-plant proteins and sodium citrate, is thus expressed in ° C.s This finding is all the more surprising since the sterilization step according to the process of the invention is carried out against what was conventionally performed by those skilled in the art for heat sterilization. Indeed, it was up until now known practice to use ultra-high temperature (UHT) sterilization, said sterilization being carried out for a period not exceeding 15 seconds at high temperature, that is to say a temperature of 135° C. to 150° C., i.e. a sterilization schedule of 2250° C.s so as not to degrade the proteins to be sterilized.

The first step of the process according to the invention thus consists in preparing an aqueous solution or suspension comprising leguminous-plant proteins and sodium citrate.

The preparation of the aqueous solution of suspension comprising leguminous-plant proteins and sodium citrate can be carried out according to the common practices of those skilled in the art. Thus, the preparation can consist in mixing, on the one hand, an aqueous solution or suspension comprising leguminous-plant proteins with, on the other hand, an aqueous solution comprising sodium citrate. The preparation can also consist in adding leguminous-plant proteins to an aqueous solution comprising sodium citrate or else in adding sodium citrate to an aqueous solution or suspension comprising leguminous-plant proteins.

The preparation of aqueous solution or suspension comprising leguminous-plant proteins and sodium citrate is advantageously carried out in such a way as to obtain a (dry/dry) ratio of weight of leguminous-plant proteins/weight of sodium citrate of between 5 and 2500. Preferably, said ratio is between 5 and 2000, preferably between 5 and 1500, more preferentially between 5 and 1000, even more preferentially between 5 and 500, 5 and 300, 5 and 100, and most particularly between 5 and 50. Even more preferentially, said ratio is between 5 and 40, and most particularly the (dry/dry) ratio of weight of leguminous-plant proteins/weight of sodium citrate is approximately 20.

According to one preferential mode, the leguminous-plant protein belongs to the family papilonaceae. In addition, according to this preferential mode, the leguminous-plant protein is chosen from the group consisting of alfalfa, clover, lupin, pea, bean, broad bean, horse bean and lentil, and mixtures thereof. More preferably, said leguminous-plant protein is chosen from the group consisting of pea, bean, broad bean and horse bean, and mixtures thereof. Even more preferably, said leguminous-plant protein is derived from pea.

The term "pea" is herein considered in its broadest accepted sense and includes in particular:
all varieties of "smooth pea" and of "wrinkled pea", and
all mutant varieties of "smooth pea" and of "wrinkled pea", this being whatever the uses for which said varieties are generally intended (food for human consumption, animal feed and/or other uses).

In the present application, the term "pea" includes the varieties of pea belonging to the *Pisum* genus and more particularly to the *sativum* and *aestivum* species.

Said mutant varieties are in particular those known as "r mutants", "rb mutants", "rug 3 mutants", "rug 4 mutants", "rug 5 mutants" and "lam mutants" as described in the article by C-L HEYDLEY et al. entitled "*Developing novel pea starches*", Proceedings of the Symposium of the Industrial Biochemistry and Biotechnology Group of the Biochemical Society, 1996, pp. 77-87.

Even more preferentially, said leguminous-plant protein is derived from smooth pea.

This is because the pea is the leguminous plant with protein-rich seeds which, since the 1970s, has been the most widely developed in Europe and mainly in France, not only as a protein source for animal feed, but also for food for human consumption.

Like all leguminous-plant proteins, pea proteins consist of three main classes of proteins: globulins, albumins and "insoluble" proteins.

The value of pea proteins lies in their good emulsifying capacities, their lack of allergenicity and their low cost, which makes them an economical functional ingredient.

Furthermore, pea proteins contribute favourably to sustainable development and their carbon impact is very positive. This is because pea cultivation is environmentally friendly and does not require nitrogenous fertilizers, since the pea fixes atmospheric nitrogen.

Thus, the leguminous-plant protein is preferably a pea protein, and particularly a pea protein isolate.

According to one embodiment, the step of preparing an aqueous solution or suspension comprising leguminous-plant proteins and sodium citrate can include the addition of one or more additives to said aqueous solution or suspension.

The additive(s) can in particular be chosen from gelling agents, soluble plant fibres, sugar, vegetable oils, polysaccharides, sodium chloride, emulsifying agents, food dyes, preservatives, sweeteners and thickeners. Preferably, the additives are chosen from gelling agents, soluble plant fibres, sugar, vegetable oils, polysaccharides, sodium chloride and emulsifying agents.

Preferably, the gelling agent is chosen from alginates, agar agar, carrageenans, arabinogalactan, gellan gum, gelatin and pectins. Preferably, the gelling agent is gellan gum.

Preferably, the soluble plant fibre is chosen from the group consisting of fructans including fructooligosaccharides (FOSs) and inulin, glucooligosaccharides (GOSs), isomaltooligosaccharides (IMOs), trans-galactooligosaccharides (TOSs), pyrodextrins, polydextrose, branched maltodextrins, indigestible dextrins and soluble oligosaccharides derived from oleaginous or protein-producing plants.

The term "soluble fibre" is intended to mean water-soluble fibres. The fibres can be quantitatively determined according to various AOAC methods. Mention may be made, by way of example, of AOAC methods 997.08 and 999.03 for fructans, FOSs and inulin, AOAC method 2000.11 for polydextrose, AOAC method 2001.03 for quantitatively determining the fibres contained in branched maltodextrins and indigestible dextrins, or AOAC method 2001.02 for GOSs and also soluble oligosaccharides derived from oleaginous or protein-producing plants.

Advantageously, the soluble plant fibre is obtained from partially hydrolysed wheat or corn starch, and contains up to 85% of total fibre.

Preferably, the vegetable oil is chosen from groundnut, avocado, borage, camelina, safflower, hemp, rapeseed, wheat germ, linseed, nigella, hazelnut, walnut, olive, evening primrose, marrow seed, grapeseed, perilla, sesame, soya bean and sunflower oils. Preferably, the vegetable oil is sunflower oil.

Preferably, the polysaccharide is chosen from gum arabic, guar gum, tara gum, microcrystalline cellulose, and carboxymethylcellulose. More preferably, the polysaccharide is guar gum.

Preferably, the emulsifying agent is chosen from lecithin, sucrose esters, fatty acid mono- and diglycerides, and sorbitan esters. Preferably, the emulsifying agent is chosen from fatty acid monoglycerides.

The process of the invention can also comprise, prior to the sterilization step, a step of homogenizing the aqueous solution or suspension comprising leguminous-plant proteins and sodium citrate, optionally also comprising one or more additives. The homogenization step can be carried out by means of the devices and techniques known to those skilled in the art, for example high-pressure homogenization, mixers, colloid mills, microbead mill homogenizers, ultrasonic homogenizers or else valve homogenizers.

According to one preferred embodiment, the homogenization is carried at high pressure. According to this embodiment, the aqueous solution or suspension comprising leguminous-plant proteins and sodium citrate is homogenized by means of a pressure of between 3 MPa and 100 MPa, preferably a pressure of between 15 MPa and 50 MPa, and most particularly at a pressure of approximately 20 MPa.

The homogenized or non-homogenized aqueous solution or suspension comprising leguminous-plant proteins and sodium citrate is subjected to a heat-sterilization step at a temperature of between 125° C. and 134° C. for a period of between 90 and 300 seconds, or at a temperature of between 135° C. and 144° C. for a period of between 90 and 210 seconds, or at a temperature of between 145° C. and 155° C. for a period of between 20 and 90 seconds.

In general, heat sterilization consists in exposing the foods to a temperature, generally greater than 100° C., for a period of time sufficient to inhibit the enzymes and any form of microorganisms, even sporulating bacteria. When the sterilization is carried out at high temperature, that is to say a temperature of 135° C. to 150° C., for a period usually not exceeding 15 seconds, i.e. a sterilization schedule of 2250° C.s, the term UHT (Ultra-High Temperature) sterilization is used. This technique has the advantage of preserving the nutritional and organoleptic quality of the product sterilized.

However, the usual conditions for UHT sterilization applied to the process according to the invention do not make it possible to reduce or mask the bitterness of the composition based on leguminous-plant proteins that is obtained.

The applicant company, to its credit, has discovered that a step of sterilizing an aqueous solution or suspension comprising leguminous-plant proteins, in particular pea proteins, by means of a particular heat treatment, combined with the use of sodium citrate, makes it possible to reduce or mask the bitterness of the composition based on leguminous-plant proteins, in particular pea proteins, that is obtained.

The heat-sterilization step can be carried out by means of the devices and techniques known to those skilled in the art.

According to the process of the present invention, the step of sterilizing the aqueous solution or suspension comprising leguminous-plant proteins and sodium citrate is carried out at a temperature of between 125° C. and 134° C. for a period of between 90 and 300 seconds, or at a temperature of between 135° C. and 144° C. for a period of between 90 and 210 seconds, or at a temperature of between 145° C. and 155° C. for a period of between 20 and 90 seconds.

The effect of a heat treatment is related to the time/temperature couple. Generally, the higher the temperature and the longer the duration, the greater the effect will be. Those skilled in the art will be able to adjust the duration of the sterilization step as a function of the temperature applied.

Particularly good results have been obtained when a particular sterilization schedule is applied. The term "sterilization schedule" is intended to mean the number obtained by multiplying the temperature applied in degrees Celsius and the contact time expressed in seconds. The number obtained, which thus represents the amount of energy applied to the aqueous solution or suspension comprising leguminous-plant proteins and sodium citrate, is thus expressed in ° C.s. Thus, when a sterilization schedule of between 8500 and 26 000° C.s, for example between 9000 and 25 200° C.s, is applied to the second step of the process according to the invention, the composition based on leguminous-plant proteins according to the invention has particularly advantageous organoleptic properties.

In one particular embodiment of the invention, the step of sterilizing the composition can be carried out at a temperature of between 125° C. and 134° C., preferably between 127° C. and 132° C., more preferably at a temperature of approximately 130° C., for a period of between 90 and 300 seconds, preferably between 100 and 280 seconds, more preferably between 110 and 250 seconds, more preferentially between 120 and 240 seconds, even more preferentially for a period of approximately 240 seconds.

In another particular embodiment, the step of sterilizing the composition can be carried out at a temperature of between 135° C. and 144° C., preferably between 137° C. and 142° C., more preferably at a temperature of approximately 140° C., for a period of between 90 and 210 seconds, preferably between 100 and 200 seconds, more preferably between 120 and 180 seconds, more preferentially for a period of approximately 180 seconds.

In another particular embodiment, the step of sterilizing the composition can be carried out at a temperature of between 145° C. and 155° C., preferably between 147° C. and 153° C., more preferably at a temperature of approximately 150° C., for a period of between 20 and 120 seconds, preferably between 30 and 120 seconds, more preferably between 30 and 70 seconds, more preferentially for a period of approximately 60 seconds. The sterilization step can also be carried out at a temperature of between 145° C. and 155° C., preferably between 147° C. and 153° C., more preferably at a temperature of approximately 150° C., for a period of between 20 and 90 seconds, preferably between 25 and 80 seconds, more preferably between 30 and 70 seconds, more preferentially for a period of approximately 60 seconds.

The sterilization step can also be carried out with a sterilization schedule of between 8500 and 26 000° C.s, for example between 9000 and 25 200° C.s, provided that a temperature of between 125° C. and 155° C. is applied for a period of between 30 and 240 seconds. The temperature can in particular be between 130 and 150° C. Another subject of the present invention relates to a reduced-bitterness composition based on leguminous-plant proteins, which can be obtained by means of the process of the invention.

Thus, the composition obtained by means of the process of the invention comprises an aqueous solution or suspension of sodium citrate and of leguminous-plant proteins with a (dry/dry) ratio of weight of leguminous proteins/weight of sodium citrate between 5 and 2500. Preferably, said ratio is between 5 and 2000, between 5 and 1500, between 5 and 1000, between 5 and 500, between 5 and 300, between 5 and 100, and most particularly between 5 and 50. Even more preferentially, said ratio is between 5 and 50, between 5 and 40, and most particularly the ratio of weight of leguminous-plant proteins/weight of sodium citrate is approximately 20. The composition according to the invention can also comprise one or more additives.

The additives can be chosen from gelling agents, soluble plant fibres, sugar, vegetable oils, polysaccharides, sodium chloride, emulsifying agents, food dyes, preservatives, sweeteners and thickeners. Preferably, the additives are chosen from gelling agents, soluble plant fibres, sugar, vegetable oils, polysaccharides, sodium chloride and emulsifying agents.

Preferably, the gelling agent is chosen from alginates, agar agar, carrageenans, arabinogalactan, gellan gum, gelatin and pectins. Preferably, the gelling agent is gellan gum.

Preferably, said soluble plant fibre is chosen from the group consisting of fructans including fructooligosaccharides (FOSs) and inulin, glucooligosaccharides (GOSs), isomaltooligosaccharides (IMOs), trans-galactooligosaccharides (TOSs), pyrodextrins, polydextrose, branched maltodextrins, indigestible dextrins and soluble oligosaccharides derived from oleaginous or protein-producing plants.

The term "soluble fibre" is intended to mean water-soluble fibres. The fibres can be quantitatively determined according to various AOAC methods. Mention may be made, by way of example, of AOAC methods 997.08 and 999.03 for fructans, FOSs and inulin, AOAC method 2000.11 for polydextrose, AOAC method 2001.03 for quantitatively determining the fibres contained in branched maltodextrins and indigestible dextrins, or AOAC method 2001.02 for GOSs and also soluble oligosaccharides derived from oleaginous or protein-producing plants.

Advantageously, the soluble plant fibre is obtained from partially hydrolysed wheat or corn starch, and contains up to 85% of total fibre.

Preferably, the vegetable oil is chosen from groundnut, avocado, borage, camelina, safflower, hemp, rapeseed, wheat germ, linseed, nigella, hazelnut, walnut, olive, evening primrose, marrow seed, grapeseed, perilla, sesame, soya bean and sunflower oils. Preferably, the vegetable oil is sunflower oil.

Preferably, the polysaccharide is chosen from gum arabic, guar gum, tara gum, microcrystalline cellulose, and carboxymethylcellulose. More preferably, the polysaccharide is guar gum.

Preferably, the emulsifying agent is chosen from lecithin, sucrose esters, fatty acid mono- and diglycerides, and sorbitan esters. Preferably, the emulsifying agent is chosen from fatty acid monoglycerides.

A third subject of the invention relates to the use of the composition based on leguminous-plant proteins, for preparing a food formulation.

In particular, the food formulation is a "ready-to-drink" beverage chosen from the group consisting of:
  beverages intended for dietetic nutrition,
  beverages intended for the nutrition of sportsmen and sportswomen,
  beverages intended for infant nutrition,
  beverages intended for clinical nutrition and/or for individuals suffering from undernourishment,
  beverages intended for the nutrition of the elderly.

The invention will be understood more clearly on reading the examples which follow, which are intended to be purely illustrative and do not in any way limit the scope of the protection.

EXAMPLES

List of the Ingredients Used:
Pea protein isolate: NUTRALYS® S85F, Roquette Freres (Lestrem, France) Soluble fibres: NUTRIOSE® FM06, Roquette Freres (Lestrem France) Gellan gum: Kelco gel HM, CP Kelco (Atlanta, Ga., USA)
Guar gum: VIDOGUM GHK 175, Unipektin Ingredients AG (Eschenz, Switzerland) Monoglycerides: TYPE P(V), C16/C18=45:55, Riken Vitamin Co. Ltd. (Tokyo, Japan).

Example 1: Effect of the Ratio of Weight of Pea Protein/Weight of Sodium Citrate This example describes the effect of the ratio of weight of pea protein/weight of sodium citrate on the improvement of the organoleptic qualities of the composition.

Seven compositions comprising pea protein were prepared with various ratios of weight of pea protein/weight of sodium citrate, according to the process below:
  preparation of an aqueous solution of pea protein, sodium citrate and additives,
  homogenization of said solution at 20 MPa,
  sterilization of the solution at 150° C. for 60 seconds.

The proportions of the various components of each of the compositions are presented in Table 1 below:

TABLE 1

| | COMPOSITIONS | | | | | | |
|---|---|---|---|---|---|---|---|
| | 1 | 2 | 3 | 4 | 5 | 6 | 7 |
| Sodium citrate | 0.000% | 0.002% | 0.004% | 0.05% | 0.19% | 0.69% | 0.87% |
| Ratio of weight of pea protein/weight of sodium citrate | — | 2200 | 1100 | 73.3 | 20 | 5.6 | 4.4 |
| Water | 1000 | 1000 | 1000 | 1000 | 1000 | 1000 | 1000 |
| Gellan gum | 0.11 | 0.11 | 0.11 | 0.11 | 0.11 | 0.11 | 0.11 |
| Sodium citrate | 0 | 0.02 | 0.04 | 0.6 | 2.2 | 7.9 | 10 |
| NUTRALYS S85F | 44 | 44 | 44 | 44 | 44 | 44 | 44 |
| NUTRIOSE FM06 | 20 | 20 | 20 | 20 | 20 | 20 | 20 |
| Sugar | 40 | 40 | 40 | 40 | 40 | 40 | 40 |
| Sunflower oil | 22 | 22 | 22 | 22 | 22 | 22 | 22 |
| Guar gum | 0.22 | 0.22 | 0.22 | 0.22 | 0.22 | 0.22 | 0.22 |

TABLE 1-continued

| | COMPOSITIONS | | | | | | |
|---|---|---|---|---|---|---|---|
| | 1 | 2 | 3 | 4 | 5 | 6 | 7 |
| Sodium chloride | 0.7 | 0.7 | 0.7 | 0.7 | 0.7 | 0.7 | 0.7 |
| Emulsifier [TYPE P(V)] | 8 | 8 | 8 | 8 | 8 | 8 | 8 |
| Total | 1135.03 | 1135.05 | 1135.07 | 1135.63 | 1137.23 | 1142.93 | 1145.03 |

Sensory tests were carried out on all of the compositions prepared, by a panel of experts, in order to evaluate 3 factors: bitterness, sweet taste and creamy aspect.

For each of the 3 factors, grades from 1 to 5 were given according to the following scale:
- bitterness: 1=bitter, 5=not bitter;
- sweet taste: 1=not sweet, 5=good sweet taste;
- creamy aspect: 1=non-creamy aspect and bad sensation in the mouth, 5=creamy aspect and good sensation in the mouth.

The results of the sensory tests are presented in Table 2 below.

TABLE 2

| | COMPOSITIONS | | | | | | |
|---|---|---|---|---|---|---|---|
| | 1 | 2 | 3 | 4 | 5 | 6 | 7 |
| Sodium citrate | 0.000% | 0.002% | 0.004% | 0.05% | 0.19% | 0.69% | 0.87% |
| Ratio of weight of pea protein/weight of sodium citrate | — | 2200 | 1100 | 73.3 | 20 | 5.6 | 4.4 |
| Bitterness | 4 | 4 | 4 | 4 | 5 | 4 | 3 |
| Sweet taste | 2 | 3 | 4 | 4 | 5 | 5 | 5 |
| Creamy aspect | 2 | 3 | 4 | 4 | 4 | 4 | 1 |

The results show that the ratio of weight of pea protein/weight of sodium citrate in the heat-sterilized composition according to the invention (Compositions 2 to 6) has an effect on the factors evaluated.

Indeed, for a ratio of weight of pea protein/weight of sodium citrate of 4.4, the composition obtained is more bitter and non-creamy compared with the compositions according to the invention.

On the other hand, the bitterness, the sweet taste and the creamy aspect are satisfactory for the compositions according to the invention in which the ratio of weight of pea protein/weight of sodium citrate is 1100, 73.3, 20 and 5.6.

This example clearly demonstrates the improvement in the organoleptic properties of the compositions based on pea proteins prepared according to the process of the invention.

Example 2: Analysis of the Effect of the UHT Sterilization Conditions

The objective of this example is to describe the effect of the UHT sterilization conditions on the organoleptic qualities of the composition. Thus, Compositions 1, 3 and 5 described in Example 1 were used to analyse the effects of varying the sterilization conditions. The amounts of the various compounds are given in Table 3:

TABLE 3

| | COMPOSITIONS | | |
|---|---|---|---|
| | 1 | 5 | 3 |
| Sodium citrate | 0.000% | 0.19% | 0.004% |
| Ratio of weight of pea proteins/weight of sodium citrate | — | 20 | 1100 |
| Water | 1000 | 1000 | 1000 |
| Gellan gum | 0.11 | 0.11 | 0.11 |
| Sodium citrate | 0 | 2.2 | 0.04 |
| NUTRALYS S85F | 44 | 44 | 44 |

TABLE 3-continued

| | COMPOSITIONS | | |
|---|---|---|---|
| | 1 | 5 | 3 |
| NUTRIOSE FM06 | 20 | 20 | 20 |
| Sugar | 40 | 40 | 40 |
| Sunflower oil | 22 | 22 | 22 |
| Guar gum | 0.22 | 0.22 | 0.22 |
| Salt | 0.7 | 0.7 | 0.7 |
| Emulsifier [TYPE P(V)] | 8 | 8 | 8 |
| Total | 1135.03 | 1137.23 | 1135.07 |

For each of the compositions, sensory tests were carried out by a panel of experts in the same way as in Example 1. The factors evaluated are the following: bitterness, sweet taste and creamy aspect.

For each of the 3 factors, grades from 1 to 5 were given according to the following scale:
- bitterness: 1=bitter, 5=not bitter;
- sweet taste: 1=not sweet, 5=good sweet taste;
- creamy aspect: 1=non-creamy aspect and bad sensation in the mouth, 5=creamy aspect and good sensation in the mouth.

The values of bitterness, sweet taste and creamy aspect may also be added to give an overall sensory value (or OSV). The higher this OSV, the better the product.

The results of the sensory tests obtained with Compositions 1, 3 and 5 are presented in Tables 4, 5 and 6, respectively.

TABLE 4

Sensory tests of the compositions not containing sodium citrate

| | | | Sterilization time | | | | | | |
|---|---|---|---|---|---|---|---|---|---|
| | | | 15 sec | 30 sec | 60 sec | 120 sec | 180 sec | 240 sec | 320 sec |
| Sterilization temperature | 150° C. | Bitterness | 1 | 3 | 4 | 3 | 1 | | |
| | | Sweet taste | 1 | 1 | 2 | 3 | 3 | | |
| | | Creamy aspect | 1 | 1 | 2 | 2 | 2 | | |
| | 140° C. | Bitterness | | 1 | 1 | 2 | 2 | 1 | |
| | | Sweet taste | | 1 | 2 | 3 | 3 | 3 | |
| | | Creamy aspect | | 1 | 2 | 3 | 3 | 3 | |
| | 130° C. | Bitterness | | 1 | 1 | 1 | 2 | 2 | 1 |
| | | Sweet taste | | 1 | 1 | 1 | 2 | 2 | 2 |
| | | Creamy aspect | | 1 | 1 | 1 | 2 | 2 | 2 |
| | 120° C. | Bitterness | | | | | | 1 | 1 |
| | | Sweet taste | | | | | | 1 | 1 |
| | | Creamy aspect | | | | | | 1 | 1 |

TABLE 5

Sensory tests of the compositions in which the ratio of weight of pea protein/weight of sodium citrate is 20

| | | | Sterilization time | | | | | | |
|---|---|---|---|---|---|---|---|---|---|
| | | | 15 sec | 30 sec | 60 sec | 120 sec | 180 sec | 240 sec | 320 sec |
| Sterilization temperature | 150° C. | Bitterness | 2 | 4 | 5 | 3 | 1 | | |
| | | Sweet taste | 2 | 4 | 5 | 5 | 5 | | |
| | | Creamy aspect | 2 | 4 | 4 | 5 | 3 | | |
| | 140° C. | Bitterness | | 2 | 2 | 4 | 5 | 1 | |
| | | Sweet taste | | 2 | 3 | 5 | 5 | 5 | |
| | | Creamy aspect | | 2 | 2 | 4 | 4 | 3 | |
| | 130° C. | Bitterness | | 1 | 1 | 4 | 5 | 5 | 1 |
| | | Sweet taste | | 1 | 1 | 5 | 4 | 5 | 5 |
| | | Creamy aspect | | 1 | 1 | 3 | 4 | 4 | 3 |
| | 120° C. | Bitterness | | | | | | 1 | 2 |
| | | Sweet taste | | | | | | 1 | 1 |
| | | Creamy aspect | | | | | | 1 | 1 |

TABLE 6

Sensory tests of the compositions in which the ratio of weight of pea protein/weight of sodium citrate is 1100

| | | | Sterilization time | | | | | | |
|---|---|---|---|---|---|---|---|---|---|
| | | | 15 sec | 30 sec | 60 sec | 120 sec | 180 sec | 240 sec | 320 sec |
| Sterilization temperature | 150° C. | Bitterness | 2 | | 4 | | 1 | | |
| | | Sweet taste | 2 | | 5 | | 4 | | |
| | | Creamy aspect | 2 | | 4 | | 3 | | |
| | 140° C. | Bitterness | | 3 | | 3 | | 1 | |
| | | Sweet taste | | 2 | | 5 | | 4 | |
| | | Creamy aspect | | 2 | | 4 | | 2 | |
| | 130° C. | Bitterness | | | 1 | | 4 | | 1 |
| | | Sweet taste | | | 1 | | 4 | | 4 |
| | | Creamy aspect | | | 1 | | 4 | | 2 |
| | 120° C. | Bitterness | | | | | | 1 | 2 |
| | | Sweet taste | | | | | | 1 | 1 |
| | | Creamy aspect | | | | | | 1 | 1 |

In the absence of sodium citrate and under the various sterilization conditions tested, the compositions always have a pronounced bitterness and a texture that is inappropriate for food use.

The UHT sterilization conditions are usually the following: 120° C. for 240 seconds, 130° C. for 20-25 seconds, 140° C. for 2 seconds, or else 150° C. for 0.1 second. Under these conditions, the compositions comprising pea protein always have a pronounced bitterness and a texture that is inappropriate for food use.

According to the results presented in Table 5, it appears that the compositions prepared according to the following sterilization conditions have a reduced bitterness and a texture that is appropriate for food use:

130° C. for 120-240 seconds,
140° C. for 120-180 seconds,
150° C. for 30-120 seconds.

This example clearly demonstrates the synergistic effect of the sterilization conditions and the presence of sodium citrate in the composition comprising pea protein on the improvement in the organoleptic properties. The compositions according to the invention have less bitterness and a better creamy aspect.

Table 7 summarises the data present in this example and presents them in a summarized manner using the Overall Sensory Value or OSV. The higher the OSV, the better the product. The OSV max value is 3×5=15 representing the perfect product. It can be seen that, for the compositions prepared at 130° C. for 120-240 s, 140° C. for 120-180 s and 150° C. for 30-120 s, the OSV of the product obtained is greater than 80% of the theoretical perfect score of 15.

These properties are thus particularly advantageous for preparing food formulations.

TABLE 7

OSV of various pea protein and sodium citrate compositions.

| T (° C.) | Tps (s) | OSV ratio 20 | OSV ratio 1100 |
| --- | --- | --- | --- |
| 150 | 15 | 6 | 6 |
| 130 | 30 | 3 | |
| 140 | 30 | 6 | 7 |
| 150 | 30 | 12 | |
| 130 | 60 | 3 | 3 |
| 140 | 60 | 7 | |
| 150 | 60 | 14 | 13 |
| 130 | 120 | 12 | |
| 140 | 120 | 13 | 12 |
| 150 | 120 | 13 | |
| 130 | 180 | 13 | 12 |
| 140 | 180 | 14 | |
| 150 | 180 | 9 | 8 |
| 120 | 240 | 3 | 3 |
| 130 | 240 | 14 | |
| 140 | 240 | 9 | 7 |
| 120 | 320 | 4 | 4 |
| 130 | 320 | 9 | 7 |

The invention claimed is:

1. A process for preparing a reduced-bitterness composition comprising leguminous-plant proteins, comprising the steps of:
    preparing an aqueous solution or suspension comprising leguminous-plant proteins and sodium citrate, in such a way as to obtain a (dry/dry) ratio of weight of leguminous-plant proteins/weight of sodium citrate of between 5 and 2500;
    heat-sterilizing said aqueous solution or suspension at a temperature of between 125° C. and 134° C. for a period of between 90 and 300 seconds, or at a temperature of between 135° C. and 144° C. for a period of between 90 and 210 seconds, or at a temperature of between 145° C. and 155° C. for a period of between 20 and 90 seconds, and
    obtaining the reduced-bitterness composition,
    wherein the leguminous-plant proteins are selected from the group consisting of pea, broad bean, horse bean, and mixtures thereof.

2. The process according to claim 1, wherein the process also comprises a step of homogenizing the aqueous solution or suspension comprising leguminous-plant proteins and sodium citrate, prior to the heat-sterilizing step of said aqueous solution or suspension.

3. The process according to claim 2, wherein the homogenization step is carried out at high pressure.

* * * * *